(12) United States Patent
Stolka et al.

(10) Patent No.: US 9,622,720 B2
(45) Date of Patent: Apr. 18, 2017

(54) ULTRASOUND SYSTEM WITH STEREO IMAGE GUIDANCE OR TRACKING

(71) Applicant: Clear Guide Medical, INC, Baltimore, MA (US)

(72) Inventors: Philipp Jakob Stolka, Baltimore, MD (US); Pezhman Foroughi, Baltimore, MD (US); Matthew C. Rendina, Baltimore, MD (US); Gregory Donald Hager, Baltimore, MD (US); Emad Mikhail Boctor, Baltimore, MD (US)

(73) Assignee: CLEAR GUIDE MEDICAL, INC., Baltimore, MD (US)

( * ) Notice: Subject to any disclaimer, the term of this patent is extended or adjusted under 35 U.S.C. 154(b) by 0 days.

(21) Appl. No.: 14/092,755

(22) Filed: Nov. 27, 2013

(65) Prior Publication Data

US 2015/0148664 A1     May 28, 2015

(51) Int. Cl.
*A61B 5/05*     (2006.01)
*A61B 8/00*     (2006.01)
(Continued)

(52) U.S. Cl.
CPC .......... *A61B 8/4254* (2013.01); *A61B 8/0841* (2013.01); *A61B 8/13* (2013.01);
(Continued)

(58) Field of Classification Search
USPC .......... 600/407, 437–472, 473–480
See application file for complete search history.

(56) References Cited

U.S. PATENT DOCUMENTS 5,144,482 A  *  9/1992  Gould ........................... 359/478
6,019,724 A     2/2000  Gronningsaeter et al.
(Continued)

FOREIGN PATENT DOCUMENTS

WO   WO 2007/113815 A2   10/2007
WO   WO2011/063266   *   5/2011   ............. A61B 19/00

OTHER PUBLICATIONS

Engineering Toolbox, "Coefficients of Linear Expansion." www.engineeringtoolbox.com/linear-expansion-coefficients-d_95.html. Dated Aug. 22, 2009 via the "WayBack Machine."*
(Continued)

*Primary Examiner* — James Kish
(74) *Attorney, Agent, or Firm* — Venable LLP; Henry J. Daley; Ilya Svetlov

(57) ABSTRACT

An image-guided ultrasound system may include an ultrasound probe, a display configured to communicate with the ultrasound probe to receive ultrasound signals to display images from the ultrasound probe, and an imaging device that may be attached to or integral with the ultrasound probe and configured to communicate with the display to display information derived from images from the imaging device. The imaging device may include a stabilization assembly, an imaging device assembly physically coupled to the stabilization assembly, a plurality of light-sensitive devices physically coupled to the stabilization assembly, and a memory unit physically coupled to the imaging device assembly, the memory unit configured to store calibration or usage information for the image-guided ultrasound system.

14 Claims, 11 Drawing Sheets

(51) Int. Cl.
A61B 8/08 (2006.01)
A61B 8/13 (2006.01)
A61B 34/20 (2016.01)

(52) U.S. Cl.
CPC .......... *A61B 8/4444* (2013.01); *A61B 8/4455* (2013.01); *A61B 8/463* (2013.01); *A61B 8/52* (2013.01); *A61B 8/5261* (2013.01); *A61B 8/58* (2013.01); *A61B 34/20* (2016.02); *A61B 8/461* (2013.01); *A61B 2034/2055* (2016.02)

(56) References Cited

U.S. PATENT DOCUMENTS

| | | |
|---|---|---|
| 6,234,969 B1* | 5/2001 | Chaintreuil et al. .......... 600/449 |
| 6,338,716 B1 | 1/2002 | Hossack et al. |
| 6,491,702 B2 | 12/2002 | Heilbrun et al. |
| 6,503,195 B1 | 1/2003 | Keller et al. |
| 6,612,991 B2 | 9/2003 | Sauer et al. |
| 6,711,429 B1 | 3/2004 | Gilboa et al. |
| 7,103,212 B2 | 9/2006 | Hager et al. |
| 7,171,255 B2 | 1/2007 | Holupka et al. |
| 7,787,992 B2 | 8/2010 | Pretlove et al. |
| 8,073,528 B2 | 12/2011 | Zhao |
| 8,303,505 B2 | 11/2012 | Webler et al. |
| 8,391,571 B2 | 3/2013 | Cinquin et al. |
| 8,517,955 B2 | 8/2013 | Keast et al. |
| 8,547,401 B2 | 10/2013 | Mallinson et al. |
| 2002/0016533 A1 | 2/2002 | Marchitto et al. |
| 2002/0077533 A1 | 6/2002 | Bieger et al. |
| 2002/0115922 A1 | 8/2002 | Waner et al. |
| 2003/0135115 A1 | 7/2003 | Burdette et al. |
| 2003/0135119 A1* | 7/2003 | Lee et al. ....................... 600/461 |
| 2003/0158503 A1 | 8/2003 | Matsumoto |
| 2004/0002657 A1* | 1/2004 | Marian .......................... 600/459 |
| 2004/0019274 A1 | 1/2004 | Galloway et al. |
| 2004/0019280 A1 | 1/2004 | Waner et al. |
| 2004/0106869 A1 | 6/2004 | Tepper |
| 2004/0152988 A1 | 8/2004 | Weirich |
| 2004/0215072 A1* | 10/2004 | Zhu ............................... 600/407 |
| 2005/0085717 A1 | 4/2005 | Shahidi |
| 2005/0182316 A1 | 8/2005 | Burdette et al. |
| 2005/0203399 A1 | 9/2005 | Vaezy et al. |
| 2007/0021670 A1 | 1/2007 | Mandelis et al. |
| 2008/0125720 A1* | 5/2008 | Kim et al. ....................... 604/177 |
| 2008/0177184 A1* | 7/2008 | Goldman et al. ............. 600/476 |
| 2008/0188749 A1 | 8/2008 | Rasche et al. |
| 2008/0266323 A1 | 10/2008 | Biocca et al. |
| 2009/0292214 A1 | 11/2009 | Ferren et al. |
| 2010/0168562 A1 | 7/2010 | Zhao et al. |
| 2010/0168763 A1 | 7/2010 | Zhao et al. |
| 2010/0298704 A1* | 11/2010 | Pelissier et al. .............. 600/443 |
| 2010/0312141 A1 | 12/2010 | Keast et al. |
| 2011/0009694 A1 | 1/2011 | Schultz et al. |
| 2011/0166450 A1 | 7/2011 | Peyrard et al. |
| 2011/0319759 A1 | 12/2011 | Liu et al. |
| 2012/0140085 A1 | 6/2012 | Gallinat et al. |
| 2012/0143049 A1 | 6/2012 | Neubauer et al. |
| 2012/0253200 A1 | 10/2012 | Stolka et al. |
| 2012/0304128 A1 | 11/2012 | Woo et al. |
| 2012/0313963 A1 | 12/2012 | Chen-Quee et al. |
| 2012/0316407 A1 | 12/2012 | Anthony et al. |
| 2013/0016185 A1 | 1/2013 | Stolka et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0331734 A1 | 12/2013 | Keast et al. |

OTHER PUBLICATIONS

Image Guided Surgical Interventions, Current Problems in Surgery, vol. 46, pp. 730-766, Sep. 2009, available at http://biorobotics.harvard.edupubs/2009/CurrentProblemsInSurgery.pdf.

Baumhauer et al., Navigation in Endoscopic Soft Tissue Surgery: Perspectives and Limitations, Journal of Endourology, Apr. 2008, 22(4): 750-766, available at http://online.liebertpub.com/doi/abs/10.1089/end.2007.9027.

Allaf et al., "Laparoscopic partial nephrectomy: evaluation of long-term oncological outcome," J Uro Sep. 2004;172(3):871-3.

Benoist et al., "Complete response of colorectal liver metastases after chemotherapy: does it mean cure?" J Clin Oncol. Aug. 20, 2006;24(24):3939-45.

Berber et al., "Resection versus laparoscopic radiofrequency thermal ablation of solitary colorectal liver metastasis," J Gastrointest Surg. Nov. 2008;12(11):1967-72.

Bijol et al., "Evaluation of the nonneoplastic pathology in tumor nephrectomy specimens: predicting the risk of progressive renal failure," Am J Surg Pathol. May 2006;30(5):575-84.

Billings et al., "A hybrid surface/image based approach to facilitate ultrasound/CT registration," accepted SPIE Medical Imaging 2011.

Boctor et al., "Prostate brachytherapy seed localization using combined photoacoustic and ultrasound imaging," SPIE Medical Imaging 2010.

Boctor et al., "Robot-assisted 3D strain imaging for monitoring thermal ablation of liver," Annual congress of the Society of American Gastrointestinal Endoscopic Surgeons, pp. 240-241, 2005.

Boctor et al., "Ultrasound Monitoring of Tissue Ablation via Deformation Model and Shape Priors," International Conference on Medical Image Computing and Computer-Assisted Intervention, MICCAI 2006.

Bonadonna et al., "Primary chemotherapy in operable breast cancer: eight-year experience at the Milan Cancer Institute," SOJ Clin. Oncol. Jan. 1998;16(1):93-100.

Chagpar et al., "Accuracy of Physical Examination, Ultrasonography and Mammography in Predicting Residual Pathologic Tumor size in patients treated with neoadjuvant chemotherapy," Annals of surgery vol. 243, No. 2, Feb. 2006.

Chen et al., "A prospective randomized trial comparing percutaneous local ablative therapy and partial hepatectomy for small hepatocellular carcinoma," Ann Surg. Mar. 2006;243(3):321-8.

Coresh et al., "Prevalence of chronic kidney disease in the United States," JAMA Nov. 7, 2007;298(17):2038-47.

Fergany et al., "Long-term results of nephron sparing surgery for localized renal cell carcinoma: 10-year followup," J Uro Feb. 2000;163(2):442-5.

Foroughi et al., "Tracked Ultrasound Elastography (TrUE)," in Medical Image Computing and Computer Integrated surgery, 2010.

Goldberg et al., "Thermal ablation therapy for focal malignancy: a unified approach to underlying principles, techniques, and diagnostic imaging guidance," AJR Am J Roentgenol. Feb. 2000;174(2):323-31.

Goldsmith et al., "An Inertial-Optical Tracking System for Portable, Quantitative, 31) Ultrasound," 2008 IEEE Ultrasonics Symposium Proceedings, Beijing, China, Nov. 2-5, 2008.

Greenleaf et al., "Selected methods for imaging elastic properties of biological tissues," Annu Rev Biomed Eng. 2003;5:57-78.

Gruenberger et al., "Importance of response to neoadjuvant chemotherapy in potentially curable colorectal cancer liver metastases," BMC Cancer. Apr. 25, 2008;8:120.

Hafez et al., "Nephron sparing surgery for localized renal cell carcinoma: impact of tumor size on patient survival, tumor recurrence and TNM staging," J Urol Dec. 1999;162(6):1930-3.

Hall et al., In vivo real-time freehand palpation imaging Ultrasound Med Biol. Mar. 2003; 29(3):427-35.

Hinshaw et al., "Multiple-Electrode Radiofrequency Ablation of Symptomatic Hepatic Cavernous Hemangioma," Am. J. Roentgenol., vol. 189, Issue 3, W-149, Sep. 1, 2007.

Hock et al., "Increasing incidence of all stages of kidney cancer in the last 2 decades in the United States: an analysis of surveillance, epidemiology and end results program data," J Urol 2002; 167:57-60. Ovid Full Text Bibliographic Links.

Hollenbeck et al., "National utilization trends of partial nephrectomy for renal cell carcinoma: a case of underutilization?" Urology Feb. 2006;67(2):254-9.

(56) References Cited

OTHER PUBLICATIONS

Huang et al., "Partial nephrectomy versus radical nephrectomy in patients with small renal tumors—is there a difference in mortality and cardiovascular outcomes?" J Uro Jan. 2009;181(1):55-61; discussion-2.
Ismail et al., "3D-guided CT reconstruction using time-of-flight camera," Accepted in SPIE Medical Imaging 2011.
Jemal et al., "Cancer statistics," 2008. CA Cancer J Clin 2008; 58:71-96. SFX.
Jemal et al., "Cancer statistics," 2007. CA Cancer J Clin Jan.-Feb. 2007;57(1):43-66.
Koichi et al., "Insufficient radiofrequency ablation therapy may induce further malignant transformation of hepatocellular carcinoma," Journal of Hepatology International, vol. 2, No. 1, Mar. 2008, pp. 116-123.
Koniaris et al., "Focal hepatic ablation using interstitial photon radiation energy," J Am Coll Surg. Aug. 2000;191(2):164-74.
Konofagou, "Quo vadis elasticity imaging?" Ultrasonics. Apr. 2004; 42(1-9):331-6.
Kunkle et al., "Excise, ablate or observe: the small renal mass dilemma—a meta-analysis and review," J Urol Apr. 2008; 179(4):1227-33; discussion 33-4.
Leibovich et al., "Nephron sparing surgery for appropriately selected renal cell carcinoma between 4 and 7 cm results in outcome similar to radical nephrectomy," J Urol Mar. 2004;171(3):1066-70.
Lyshchik et al., "Thyroid gland tumor diagnosis at US elastography," Radiology. Oct. 2005;237(1):202-11.
Moinzadeh et al., "'Laparoscopic partial nephrectomy: 3-year followup,'" J Urol Feb. 2006;175(2):459- 62.
Mulier et al., "Local recurrence after hepatic radiofrequency coagulation: multivariate meta-analysis and review of contributing factors," Ann Surg. Aug. 2005;242(2):158-71.
Ophir et al., "Elastography: a quantitative method for imaging the elasticity of biological tissues," Ultrasonic Imag.,13:111-134, 1991.
Partridge et al., "Accuracy of MR imaging for revealing residual breast cancer in patients who have undergone neoadjuvant chemotherapy," AJR Am J Roentgenol. Nov. 2002; 179(5):1193-9.
Poon et al., "Learning curve for radiofrequency ablation of liver tumors: prospective analysis of initial 100 patients in a tertiary institution," Ann Surg. Apr. 2004; 239(4):441-9.
Purohit et al., "Imaging clinically localized prostate cancer," Urol Clin North Am. May 2003;30(2):279-93.
Rivaz et al., "Ablation monitoring with elastography: 2D in-vivo and 3D ex-vivo studies," International Conference on Medical Image Computing and Computer-Assisted Intervention, MICCAI 2008.
Rivaz et al., "Tracked Regularized Ultrasound Elastography for Targeting Breast Radiotherapy," Medical Image Computing and Computer Assisted Intervention (MICCAI) 2009.

Rosen et al., "Accuracy of MRI in the detection of residual breast cancer after neoadjuvant chemotherapy," AJR Am J Roentgenol. Nov. 2003; 181(5):1275-82.
Scott et al., "Accuracy and effectiveness of laparoscopic vs open hepatic radiofrequency ablation," Surg Endosc. Feb. 2001;15(2):135-40.
Smith et al., "Positron emission tomography using [(18)F]-fluorodeoxy-D-glucose to predict the pathologic response of breast cancer to primary chemotherapy," J Clin Oncol. Apr. 2000;18(8):1676-88.
Stolka et al., "A 3D-elastography-guided system for laparoscopic partial nephrectomies". SPIE Medical Imaging 2010 (San Diego, CA/USA) 76251-12.
Thompson et al., "Radical nephrectomy for pT1a renal masses may be associated with decreased overall survival compared with partial nephrectomy," J Uro Feb. 1, 2008; 179(2):468-71; discussion 72-3.
Valero et al., "Locally Advanced Breast Cancer," Oncologist. 1996; 1(1 & 2):8-17.
Van Duijnhoven et al., "Factors influencing the local failure rate of radiofrequency ablation of colorectal liver metastases," Ann Surg Oncol. May 2006; 13(5):651-8. Epub Mar. 17, 2006.
Varghese et al., Elastographic imaging of thermal lesions in liver in-vivo using diaphragmatic stimuli. Ultrason Imaging. Jan. 2004;26(1):18-28.
Volpe et al., "The natural history of incidentally detected small renal masses," Cancer Feb. 15, 2004;100(4):738-45.
Volpe et al., "The natural history of small renal masses," Nat Clin Pract Urol 2005; 2:384-390.
Wood et al., "Radiofrequency ablation of 231 unresectable hepatic tumors: indications, limitations, and complications," Ann Surg Oncol. Sep. 2000;7(8):593-600.
Xu et al., "Statistical Projection Completion in X-ray CT Using Consistency Conditions," Medical Imaging, IEEE Transactions on , vol. 29, No. 8, pp. 1528-1540, Aug. 2010.
Zini et al., "Radical versus partial nephrectomy: effect on overall and noncancer mortality," Cancer Apr. 1, 2009;115(7):1465-71.
Stolka et al. "Navigation with local sensors in handheld 3D ultrasound: initial in-vivo experience," SPIE Medical Imaging 2011, Lake Buena Vista, FL/USA, pp. 79681J-79681J, International Society for Optics and Photonics, 2011.
Wang et al. "The Kinect as an interventional tracking system," SPIE Medical Imaging, San Diego, CA, USA, pp. 83160U-83160U, International Society for Optics and Photonics, 2012.
E.M. Petriu "Absolute Position Measurement Using Pseudo-Random Binary Encoding" School of Information Technology and Engineering, University of Ottawa, available at http://www.csi.uottawa.ca/~petriu/ELG5161-PRBS-encoding.pdf.
International Search Report and Written Opinion issued in PCT Application No. PCT/US2014/067411 dated Mar. 17, 2015.

* cited by examiner

ULTRASOUND SYSTEM WITH STEREO IMAGE GUIDANCE OR TRACKING

BACKGROUND

1. Field of Invention

The field of the currently claimed embodiments of this invention relate to imaging devices, and more particularly to imaging devices with one or more sensors for observation and tracking of one or more tools.

2. Discussion of Related Art

In image-guided interventions, the tracking and localization of imaging devices and medical tools during procedures are exceptionally important and are considered the main enabling technology in image-guided surgery (IGS) systems. Tracking technologies may be categorized into the following groups: 1) mechanical-based tracking including active robots (e.g., DaVinci robot) and passive-encoded mechanical arms (e.g., Faro mechanical arms), 2) optical-based tracking, 3) acoustic-based tracking, and 4) electromagnetic (EM)-based tracking.

Ultrasound is one useful imaging modality for image-guided interventions including ablative procedures, biopsy, radiation therapy, and surgery. In the literature and in research labs, ultrasound-guided intervention research is performed by integrating a tracking system (either optical or EM methods) with an ultrasound (US) imaging system to, for example, track and guide liver ablations, or in external beam radiation therapy [E. M. Boctor, M. DeOliviera, M. Choti, R. Ghanem, R. H. Taylor, G. Hager, G. Fichtinger, "Ultrasound Monitoring of Tissue Ablation via Deformation Model and Shape Priors", International Conference on Medical Image Computing and Computer-Assisted Intervention, MICCAI 2006; H. Rivaz, I. Fleming, L. Assumpcao, G. Fichtinger, U. Hamper, M. Choti, G. Hager, and E. Boctor, "Ablation monitoring with elastography: 2D in-vivo and 3D ex-vivo studies", International Conference on Medical Image Computing and Computer-Assisted Intervention, MICCAI 2008; H. Rivaz, P. Foroughi, I. Fleming, R. Zellars, E. Boctor, and G. Hager, "Tracked Regularized Ultrasound Elastography for Targeting Breast Radiotherapy", Medical Image Computing and Computer Assisted Intervention (MICCAI) 2009]. Current commercial systems may include integrating an EM tracking device into high-end cart-based US system. Small EM sensors may be integrated into the ultrasound probe, and similar sensors may be attached and fixed to the intervention tool of interest.

Limitations of the current approach on both the research and commercial sides may be attributed to the available tracking technologies and to the feasibility of integrating these systems and using them in clinical environments. For example, mechanical-based trackers are considered expensive and intrusive solutions, i.e. they require large space and limit user motion. On the other hand, acoustic tracking does not provide sufficient navigation accuracy. Optical and EM tracking technologies require intrusive setups with a base camera (in case of optical tracking methods) or a reference EM transmitter (in case of EM methods). Additionally, optical rigid-body or EM sensors have to be attached to the imager and all needed tools, hence offline calibration and sterilization steps are required. Thus, there remains a need for improved imaging devices for use in image-guided surgery.

SUMMARY

Aspects of the invention may involve systems, devices, and methods. In one embodiment, an image-guided ultrasound system may be provided. The system may include an ultrasound probe; a display configured to communicate with the ultrasound probe to receive ultrasound signals to display images from the ultrasound probe; and an imaging device at least one of attached to or integral with said ultrasound probe and configured to communicate with the display to display information derived from images from the imaging device. The imaging device may include a stabilization assembly, an imaging device assembly physically coupled to the stabilization assembly, a plurality of light-sensitive devices physically coupled to the stabilization assembly, and a memory unit physically coupled to the imaging device assembly, the memory unit configured to store at least one of calibration or usage information for the image-guided ultrasound system.

In another embodiment, a method for performing an image-guided procedure may be provided. The method may include scanning a region of interest with an image-guided ultrasound probe; receiving ultrasound data from said image-guided ultrasound probe of a peripheral region proximate said region of interest, said image-guided ultrasound probe comprising a plurality of light-sensitive devices attached at fixed positions relative to an ultrasound probe; employing a tool for use within said region of interest and within said peripheral region such that at least a portion of said tool is visible to the plurality of light-sensitive devices; and at least one of tracking or guiding said tool during said image-guided procedure based on imaging information from the plurality of light-sensitive devices, wherein the plurality of light-sensitive devices are attached to a stabilization assembly to prevent movement between the plurality of light-sensitive devices, and wherein said image-guided ultrasound probe further comprises a memory unit configured to store at least one of calibration or usage data.

In yet another embodiment, an image-guiding device for image-guided surgery may be provided. The device may include a support structure; a stabilization assembly coupled support structure; and a first light-sensitive device and a second light-sensitive device coupled to the stabilization assembly, wherein the stabilization assembly prevents movement between the first light-sensitive device and the second light-sensitive device, the first light-sensitive device and the support structure, and the second light-sensitive device and the support structure.

BRIEF DESCRIPTION OF THE DRAWINGS

Further objectives and advantages will become apparent from a consideration of the description, drawings, and examples.

DETAILED DESCRIPTION

Figure 1:
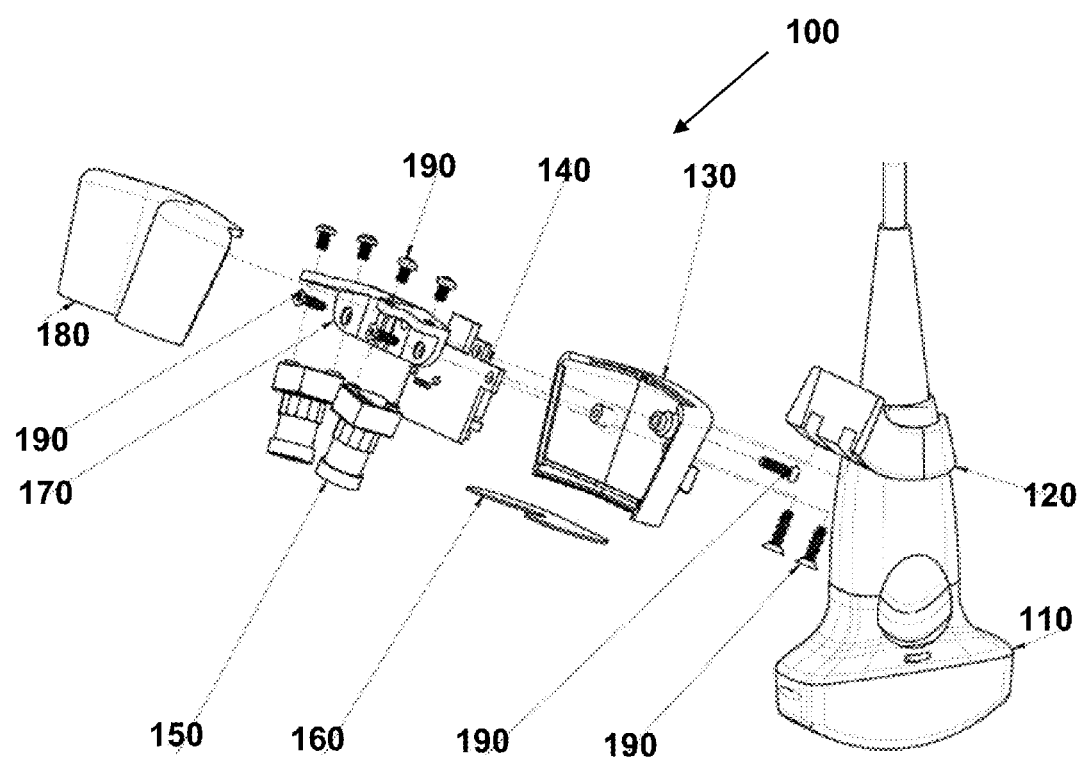
FIG. 1 shows an embodiment of an imaging component for an imaging system according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of this invention describe IGI-(image-guided interventions)-enabling "platform technology" going beyond the current paradigm of relatively narrow image-guidance and tracking. It simultaneously aims to overcome limitations of tracking, visualization, and guidance; specifically using and integrating techniques e.g. related to needle identification and tracking using 3D computer vision and structured light; and imaging device tracking using local sensing approaches; among others. Examples of IGI may be seen in U.S. patent application Ser. No. 13/511,101, titled "Low-cost image-guided navigation and intervention systems using cooperative sets of local sensors," published as U.S. Patent Application Publication No. 2013/0016185. The contents of which are incorporated herein incorporated by reference in their entirety.

The current invention covers a wide range of different embodiments, sharing a tightly integrated common core of components and methods used for general imaging, projection, vision, and local sensing.

Some embodiments of the current invention are directed to combining a group of complementary technologies to provide a local sensing approach that can provide enabling technology for the tracking of medical imaging devices, for example, with the potential to significantly reduce errors and increase positive patient outcomes. This approach can provide a platform technology for the tracking of ultrasound probes and other imaging devices, intervention guidance, and information visualization according to some embodiments of the current invention. By combining ultrasound imaging with image analysis algorithms and probe-mounted light-sensitive devices, independent optical-inertial sensors, according to some embodiments of the current invention, it is possible to reconstruct the position and trajectory of surgical needles and other tools or objects by incrementally tracking their current motion.

Some embodiments of the current invention allow the segmentation, tracking, and guidance of needles and other tools (using visual, ultrasound, and/or other imaging and localization modalities).

Such devices can allow imaging procedures with improved sensitivity and specificity as compared to the current state of the art. This can open up several possible application scenarios that previously required harmful X-ray/CT or expensive MRI imaging, and/or external tracking, and/or expensive, imprecise, time-consuming, or impractical hardware setups, or that were simply afflicted with an inherent lack of precision and guarantee of success, such as: biopsies, RF/HIFU ablations etc.: can allow 2D- or 3D-ultrasound-based needle guidance, brachytherapy: can allow 3D-ultrasound acquisition and needle guidance for precise brachytherapy seed placement, other applications relying on tracked imaging and tracked tools.

Some embodiments of the current invention may provide several advantages over existing technologies, such as combinations of: low-cost tracking, local, compact, and non-intrusive solution—ideal tracking system for hand-held and compact ultrasound systems that are primarily used in intervention and point-of-care clinical suites, but also for general needle/tool tracking under visual tracking in other interventional settings.

For example, some embodiments of the current invention are directed to devices and methods for the tracking of ultrasound probes and other imaging devices. By combining ultrasound imaging with image analysis algorithms and probe-mounted light-sensitive devices it is possible to reconstruct the position and trajectory of tools (e.g., needles, pointers, biopsy tools, laparoscopes, ablation devices, surgical instruments, or elongated tools) and other objects by incrementally tracking their current motion according to an embodiment of the current invention. This can provide several possible application scenarios that previously required expensive, imprecise, or impractical hardware setups. For example, 3D ultrasound-based needle guidance.

Current sonographic procedures mostly use handheld 2D ultrasound (US) probes that return planar image slices through the scanned 3D volume (the "region of interest" (ROI)). For percutaneous interventions requiring tool guidance, prediction of the tool trajectory is currently based on tracking with sensors attached to the distal (external) tool end and on mental extrapolation of the trajectory, relying on the operator's experience. An integrated system with 3D ultrasound, tool tracking, tool trajectory prediction and interactive user guidance would be highly beneficial.

FIG. 1 shows an embodiment of an imaging component 100 for an imaging system according to an embodiment of the current invention. Imaging component 100 includes an imaging tool 110, bracket 120 that is structured to be attachable to imaging tool 110. In the example of FIG. 1, the imaging tool 110 is an ultrasound probe and bracket 120 is structured to be attached to a probe handle of the ultrasound probe. Ultrasound probes may include, for example, Ultrasonix #C5-2. However, the broad concepts of the current invention are not limited to only this example. The bracket 120 can be structured to be attachable to other handheld instruments for image-guided surgery, such as surgical orthopedic power tools or stand-alone handheld brackets, for example. In other embodiments, the bracket 120 can be structured to be attachable to the C-arm of an X-ray system or an MRI system, for example.

Imaging component 100 may include top shell 180 and bottom shell 130 that may be coupled together to form a head shell. Top shell 180 and bottom shell 130 may be coupled securely to stabilization assembly 170 (e.g., stabilization bar). Head shell may house stabilization assembly 170 and other components of imaging component 100. Screws 190 may be used to couple the components of imaging component 100.

Imaging component 100 may also include one or more light-sensitive devices 150 (e.g., cameras, PSDs (position-sensitive devices), reflection-based laser sensing, etc.) securely attached to stabilization assembly 170. The one or more light-sensitive devices 150 may be at least one of a visible-light camera, an infra-red camera, a time-of-flight camera, a PSD (position-sensitive device), and/or a reflection-based laser sensing device in some embodiments of the current invention. The one or more light-sensitive devices 150 may be arranged to observe a surface region close to and during operation of the imaging component 100. In FIG. 1, the one or more light-sensitive devices 150 may be arranged and configured for stereo observation of a region of interest.

Imaging component 100 may also include a printed circuit board 140 that may include one or more microprocessors, one or more light sources lights, and a memory device. The light sources may include one or more LEDs, CFLs (compact fluorescent lamp), incandescent bulbs, and/or lasers. The light source may emit light in the visible spectrum, infrared, ultraviolet, or other spectrum. The printed circuit board may also be connected to one or more light-sensitive devices 150, the light source, and the memory device, and may be securely coupled to stabilization assembly 170.

Imaging component 100 may also include lens 160 that provides a screen for one or more light-sensitive devices 150. In one embodiment, lens 160 may be made of ultra-tough gorilla glass of 0.031" thickness. Lens 160 may be frosted or partially frosted to diffuse the light emitted from the light source.

Figure 2:
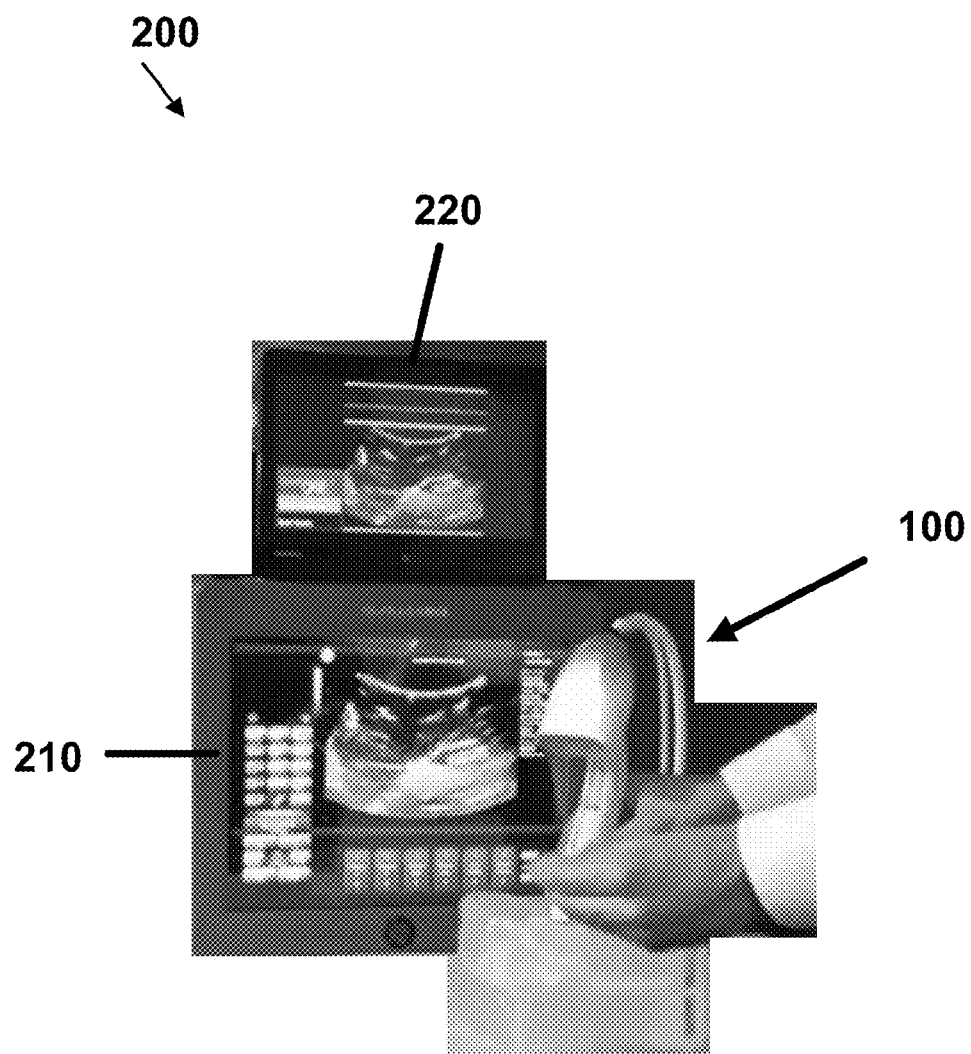
FIG. 2 shows another embodiment of an imaging system according to an embodiment of the current invention.

FIG. 2 shows an embodiment of imaging system 200 according to an embodiment of the current invention. Imaging system 200 includes imaging component 100 being controlled by a user. The user is also inserting a tool. Imaging system 200 includes image display 210. Image display may 210 display output from imaging tool 110 such as sonogram images. Imaging system 200 also includes augmented display 220. Augmented display 220 may be a touch screen and allow input from the user. Augmented display 220 may overlay tracking information on top of output from imaging tool 110. Tracking information may include current tracking status, current location, and/or current insertion depth of the tool being inserted by the user. Overlaid information may also include tool tip location and tool tip distance to a selected target.

Figure 3:
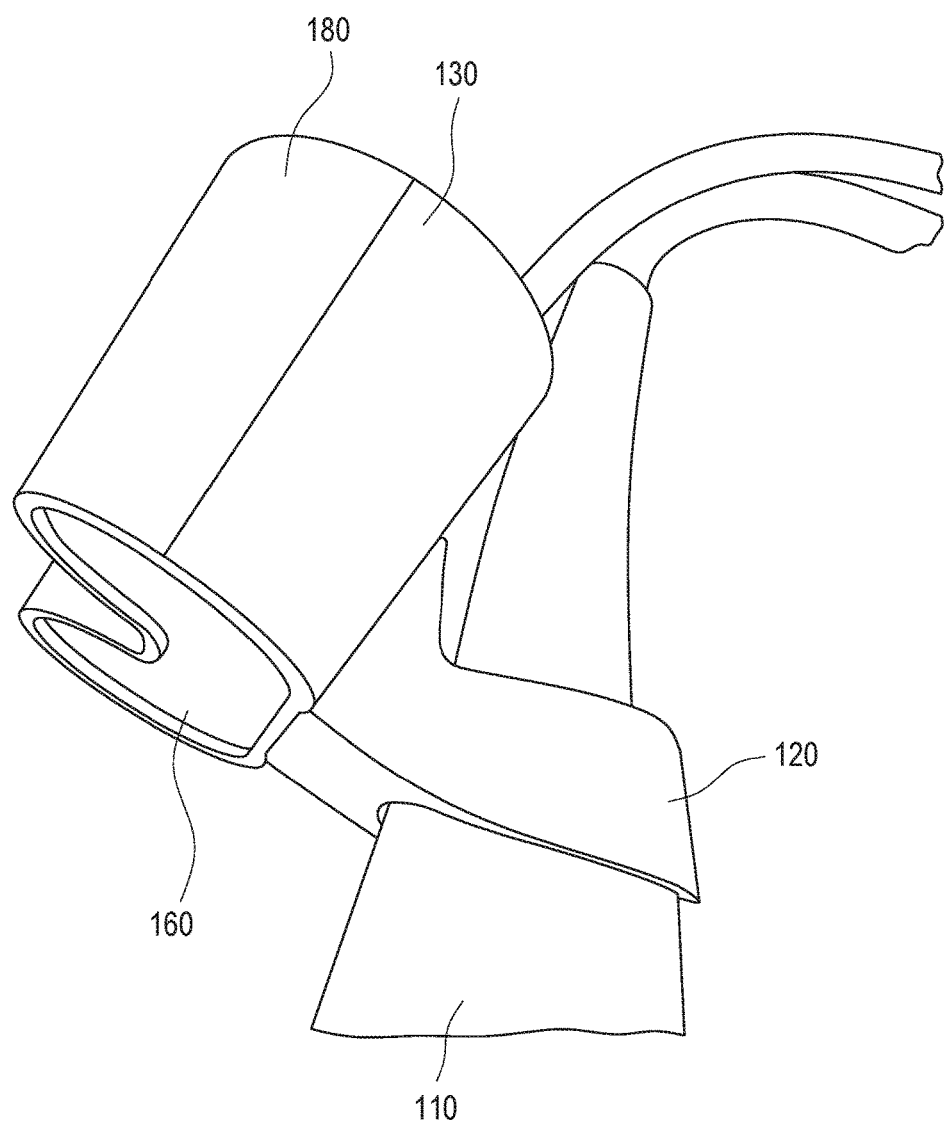
FIG. 3 shows another embodiment of an imaging component for an imaging system according to an embodiment of the current invention.

FIG. 3 shows another embodiment of an imaging component for an imaging system according to an embodiment of the current invention. In particular, FIG. 3 shows bracket 120 connected to imaging tool 110. Bracket 120 is also connected to bottom shell 130. Bottom shell 130 is connected to top shell 180. Lens 160 may be secured in place between bottom shell 130 and top shell 180.

Although FIGS. 1-3 illustrate the imaging system as an ultrasound imaging system and that the bracket 120 is structured to be attached to an imaging tool 110 as an ultrasound probe, the broad concepts of the current invention are not limited to this example. The bracket may be structured to be attachable to other imaging systems, such as, but not limited to, x-ray and magnetic resonance imaging systems, for example.

Figure 4:
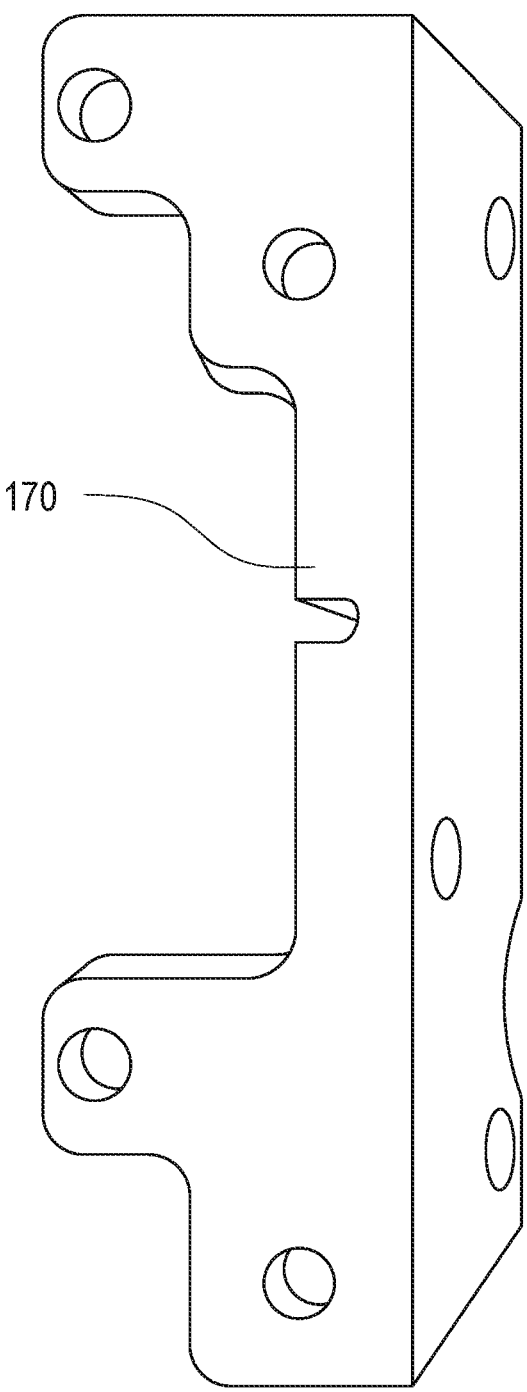
FIG. 4 shows an embodiment of a stabilization assembly for an imaging component for an imaging system according to an embodiment of the current invention.

FIG. 4 depicts an example stabilization assembly 170 that may be used in imaging component 100 in imaging system 200. Stabilization assembly 170 may be made out of a material with a low co-efficient of expansion to prevent/minimize movement between the light-sensitive devices and/or between the light-sensitive devices and the imaging device. In some embodiments a co-efficient of thermal expansion between 4-120 [10^-6 m/mK] may be sufficient. In another embodiment, a co-efficient of expansion less than 73.8 [10^-6 m/mK] (ABS (Acrylonitrile butadiene styrene) thermoplastic, or more generally 4-120 [10^-6 m/mK] (plastics), or more specifically 22.2 [10^-6 m/mK] (Aluminium) may be used. In one embodiment, stabilization assembly 170 may be made out of aluminum, stainless steel, titanium, ceramic, plastic, ABS (Acrylonitrile butadiene styrene) thermoplastic etc. The stabilization assembly may be an integral part of the imaging device assembly itself.

Figure 5:
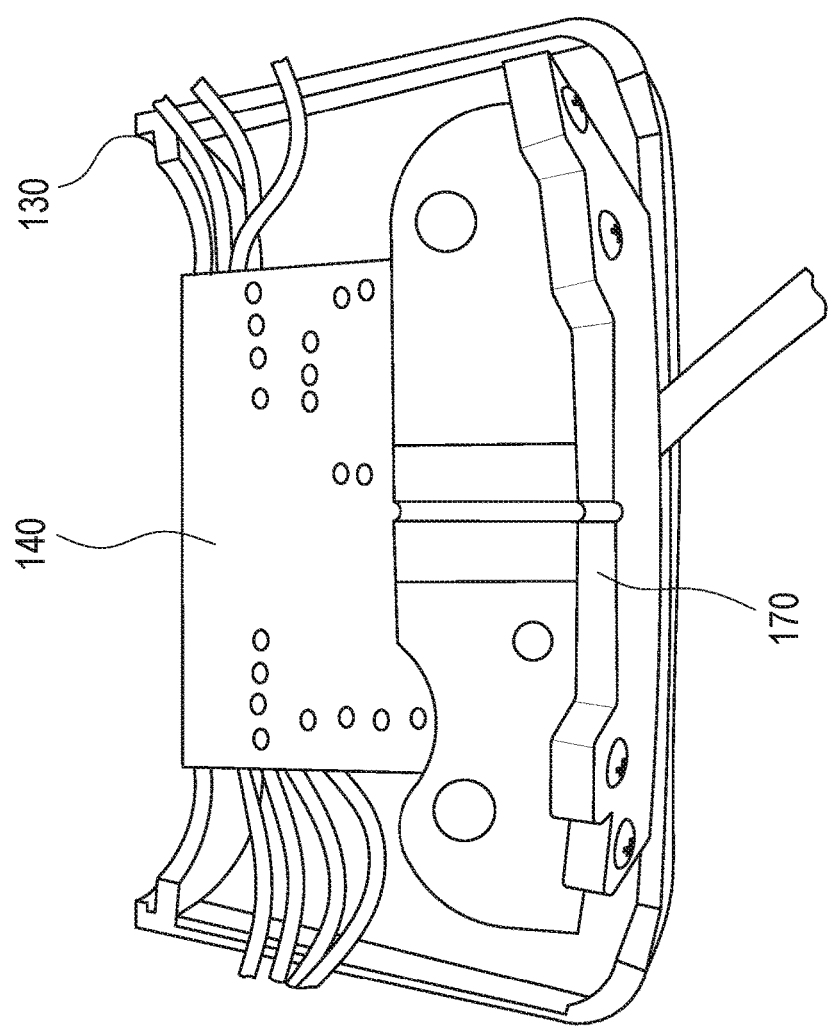
FIG. 5 shows an embodiment of an imaging component including a stabilization assembly according to an embodiment of the current invention.

FIG. 5 shows an embodiment of imaging component 100 including stabilization assembly 170 according to an embodiment of the current invention. Stabilization assembly 170 may be attached to printed circuit board 140. Stabilization assembly 170 may also be attached to bottom shell 130.

Figure 6:
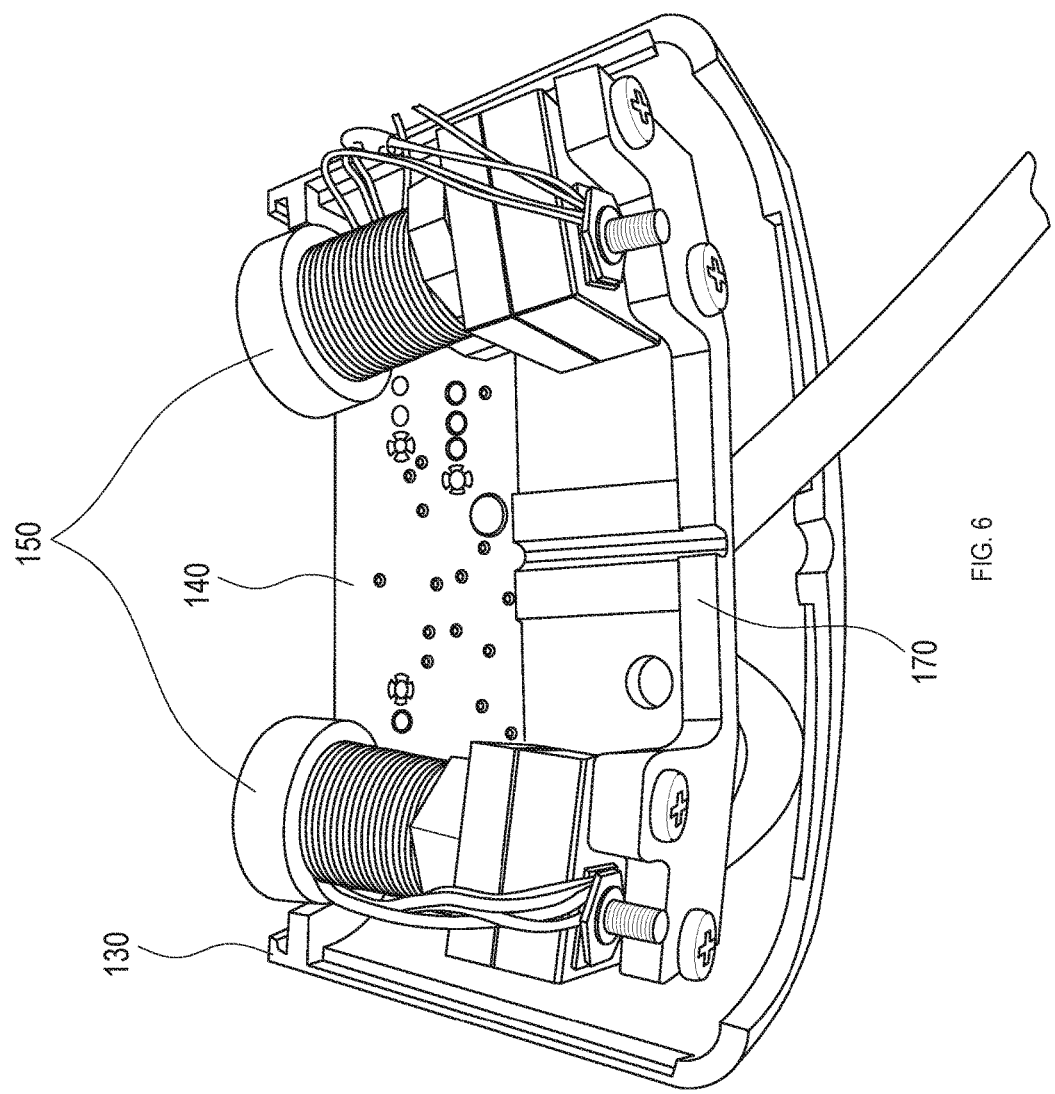
FIG. 6 shows an embodiment of an imaging component including light-sensitive devices and a printed circuit board connected to a stabilization assembly for an imaging system according to an embodiment of the current invention.

FIG. 6 shows an embodiment of imaging component 100 including light-sensitive devices 150 and printed circuit board 140 connected to stabilization assembly 170 for imaging system 200 according to an embodiment of the current invention. Stabilization assembly 170 may be securely and/or rigidly connected to bottom shell 130 and/or light-sensitive devices 150. Stabilization assembly 170 may prevent movement between light-sensitive devices 150 and between light-sensitive devices 150 and within imaging component 100. Further, Stabilization assembly 170 may prevent movement between light-sensitive devices 150 and imaging device 110.

Figure 7:
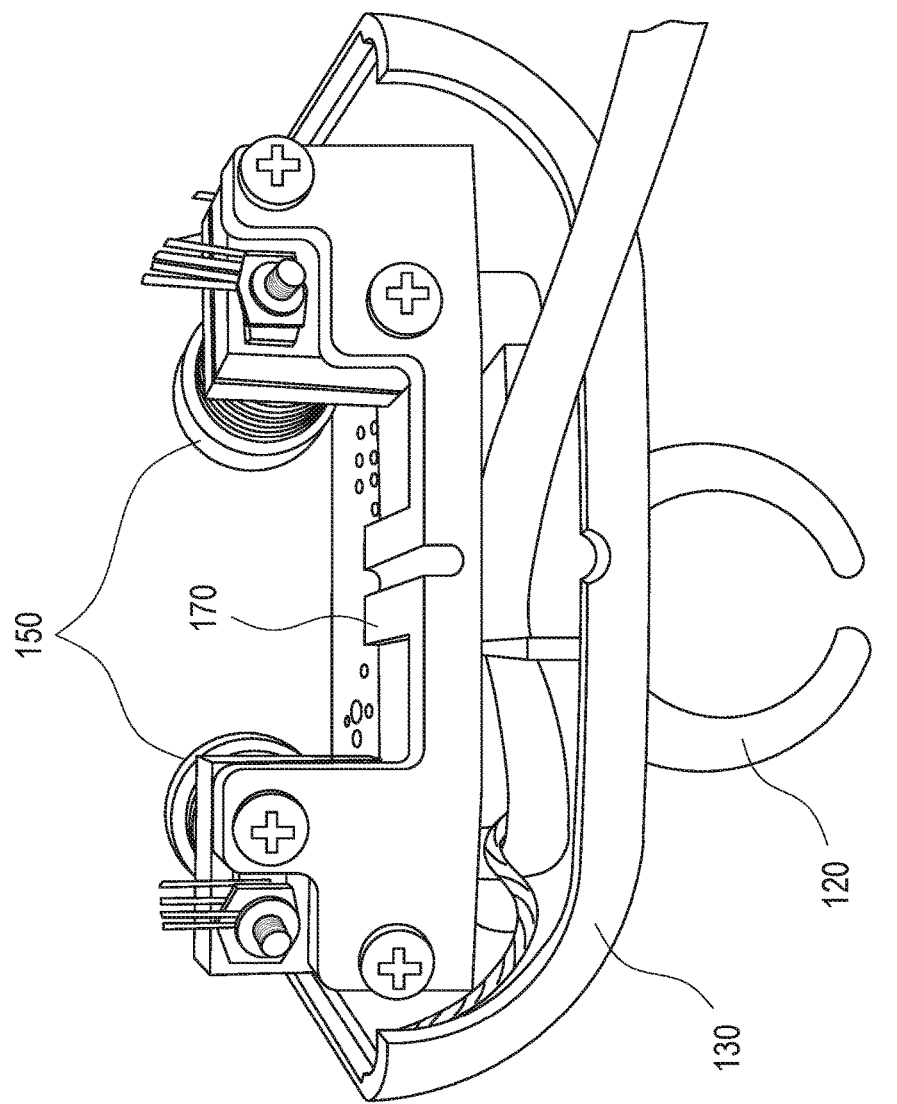
FIG. 7 shows another embodiment of an imaging component for an imaging system according to an embodiment of the current invention.

FIG. 7 shows another embodiment of imaging component 100 including light-sensitive devices 150 and bottom shell 130 connected to stabilization assembly 170. FIG. 7 also depicts bracket 120 connected to bottom shell 130.

Figure 8:
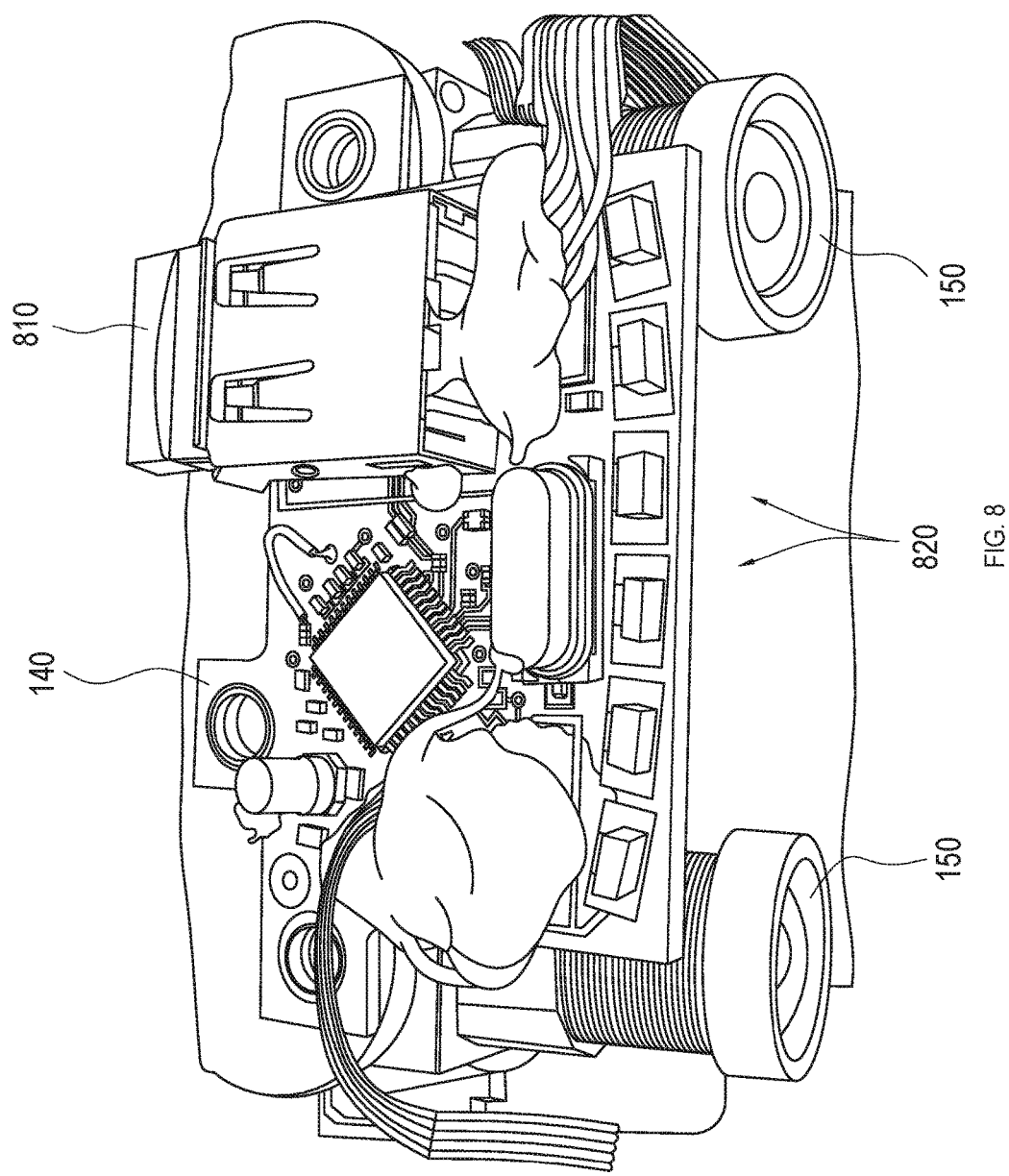
FIG. 8 shows an embodiment of an imaging component including light-sensitive devices, memory, and a light source for an imaging system according to an embodiment of the current invention.

FIG. 8 shows a shows an embodiment of imaging component 100 including light-sensitive devices 150, memory device 810, and light source 820 for imaging system 200 according to an embodiment of the current invention. FIG. 8 depicts printed circuit board 140 providing a controller for light-sensitive devices 150, light source 820, and memory device 810. Light source 820 may include any number of light sources (e.g., 6 LEDs as shown in FIG. 8). The more LEDs or other light sources the less likely shadows will interfere in object tracking. Light source 820 may output light in the visible spectrum or in other spectrums such as the infrared spectrum. Lens 160 may diffuse and/or filter the light from light source 820. Frosted or etched glass may be used for lens 160 to diffuse the light from light source 820. The more diffuse the light from light source 820, the less likely shadows will interfere in object tracking. Lens 160 may also act as a filter to prohibit light of a particular spectrum from exiting and/or entering imaging component 100. Accordingly, lens 160 may filter incoming light for light-sensitive devices 150 and/or outputted light for light source 820. Memory device 810 may include a memory card reader and/or a memory card. The memory card reader may be capable of reading and housing the memory card. In another embodiment, memory device 810 may include a flash drive. In another embodiment, memory device 810 may be a USB drive. Memory device 810 may store at least one of licensing data, configuration data, imaging device usage time, imaging device licensing information, imaging device configuration information, imaging device calibration information, and/or system software updates. Imaging device 100 may measure the amount of time an object has been tracked and may store the information in memory device 810. Calibration information may include, for example, the relative position between light-sensitive devices 150, and/or the relative position between light-sensitive devices 150 and imaging tool 110. Licensing information may include the amount of image tracking time available for imaging component 100. Imaging system 200 may produce an alert when total tracking time is some percentage (e.g. 100%, 90%, etc.) of the licensed time. Licensing time may also be an amount of time until imaging component 100 should be recalibrated (e.g., number of elapsed calendar days or if a specific calendar date has been reached).

In one embodiment, imaging system 200 may include, for example, an ultrasound probe (e.g., imaging tool 110) and one or more displays (e.g., 210 and 220). A first display (e.g., 210) may be configured to communicate with the ultrasound probe to receive ultrasound signals and display images from the ultrasound probe. An imaging device (e.g., imaging component 100) may be at least one of attached to or integral with the ultrasound probe and the imaging device may be configured to communicate with a second display (e.g., 220) to display images from the imaging device and, in some embodiments, images from the ultrasound probe. The first and second display may be the same display. Similarly, the processing units that provide the data to be displayed on the one or more displays may be separate (two or more units) or integrated (one unit). The imaging device (e.g., 100) may include stabilization assembly 170 (or other stabilization assembly), an imaging device assembly (e.g., 180 and 130) physically coupled to the stabilization assembly, a plurality of light-sensitive devices (e.g., 150) physically coupled to the stabilization assembly, and a memory unit (e.g., 810) physically coupled to the imaging device assembly (e.g., head shell). The memory unit may be configured to store calibration information and/or usage information for the image-guided ultrasound system.

Figure 11:
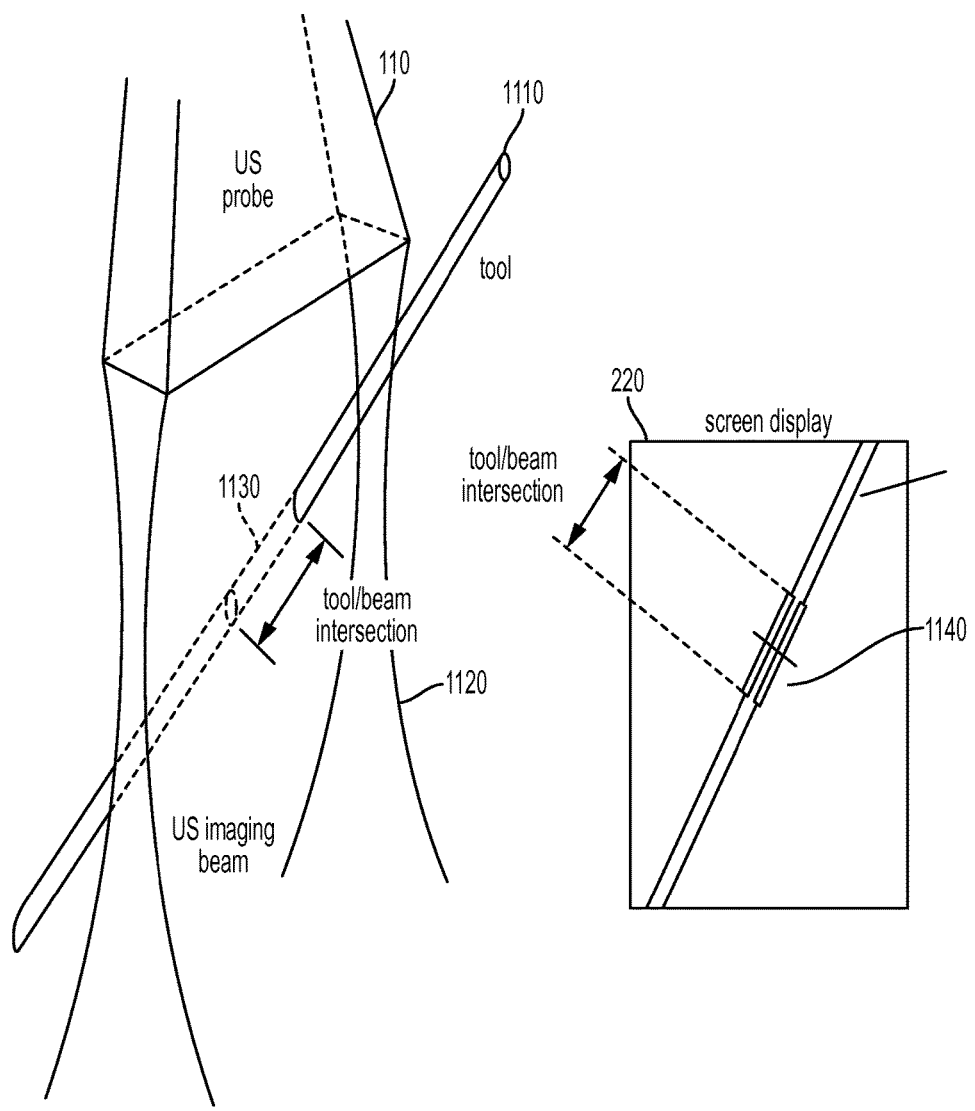
FIG. 11 illustrates an intersection of a tool and an ultrasound beam according to an embodiment.

Imaging system 200 may include an image processing module including one or more integrated circuits and/or microprocessors. The image processing module may be located on printed circuit board 140 (or another circuit in the image processing module) and/or may be located externally to imaging component 100 (e.g., an external computer or processing module). FIG. 11 illustrates the intersection of a tool 1110 and ultrasound beam 1120 from imaging tool 110 as an ultrasound probe. The image processing module may execute instructions for tracking a medical tool 1110 (e.g., a needle, a pointer, a biopsy tool, a laparoscope, an ablation device, a surgical instrument, or an elongated tool). Image processing module may first register the tool with the imaging device, where the position of the tool 1110 is known with respect to the imaging device. A representation of tool 1110 may be presented on display 220. The processing module may receive a selection of a target (e.g., a tumor, a vessel, a suspicious lesion, or other clinically relevant sites) in the images from the ultrasound probe, or may receive the target selection based on other imaging data introduced into the system (such as pre-defined target sites in CT or MRI data, later to be registered to the imaging device). The selection may be received from a touchscreen displaying the ultrasound images, for example. The module may also track the tool, display a representation of the tool in the display as the tool is being tracked; indicate a tool tip in the display (e.g., though the use of one or more perpendicular lines, pointed line arrangements, and/or color variations); calculate a distance between the tool tip and the target; output audio, wherein the audio changes based on the calculated distance between the tool tip and the target; display the calculated distance between the tool tip and the target; output visual cues as to the quality of the tool tracking; and/or indicating a loss of tool tracking though audio or visual cues. The processing module may further display the tracked tool as a line; and may represent the quality of the tool tracking as a function of a length of the displayed line. In a specific example of a tracked tool 1110 intersecting the ultrasound imaging area at 1130, there may be a certain segment of the tool 1110 physically contained within the volume of the ultrasound beam 1120. The length of this segment can be computed by the processing module based on knowledge about the standard beam shape, and may be displayed as overlaid variations in color or length or as overlaid markers 1140 on the displayed tool representation itself.

Figure 9:
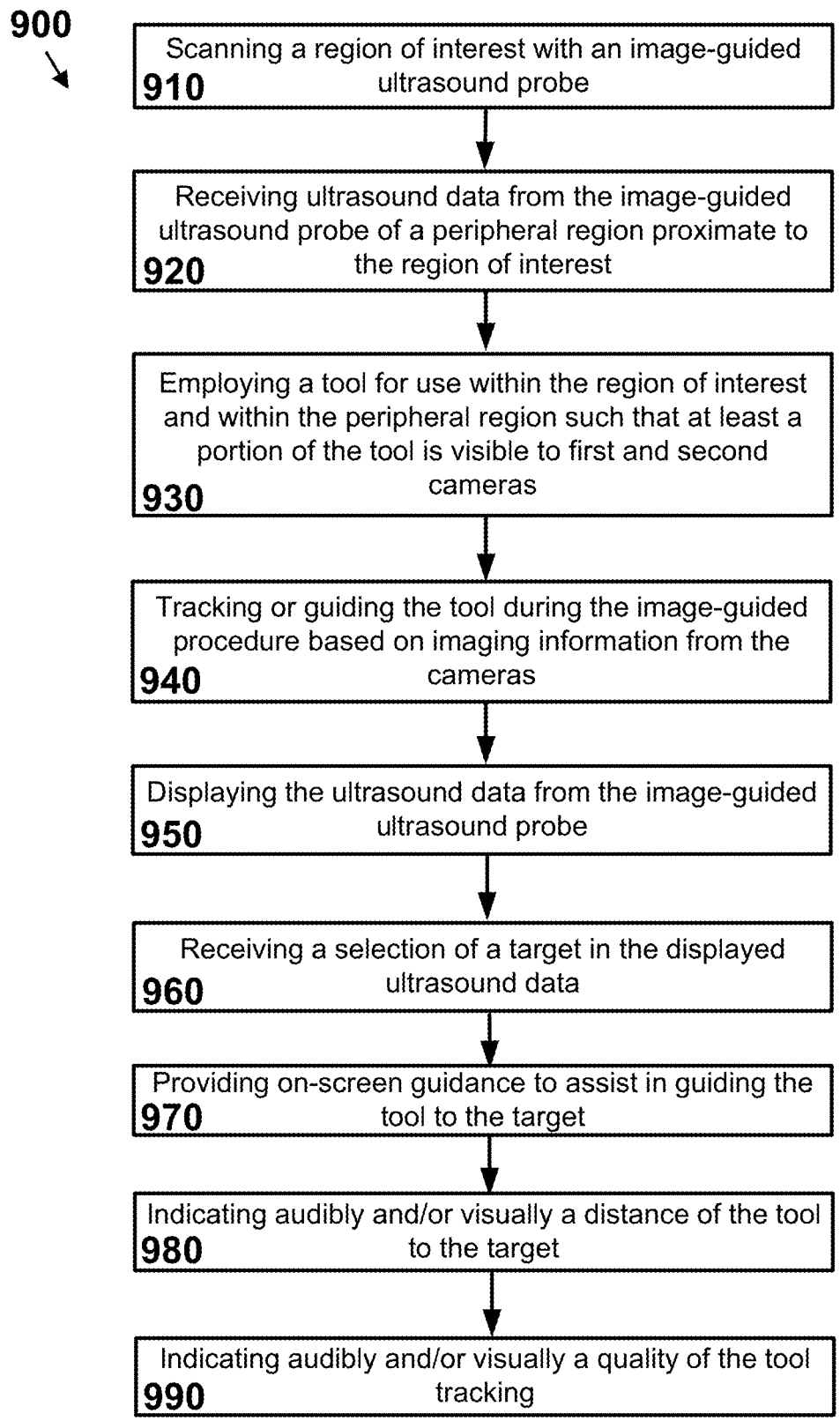
FIG. 9 depicts an example workflow according to an embodiment of the current invention.

FIG. 9 depicts an example workflow describing an image-guided procedure according to an embodiment of the current invention. In 910, a region of interest may be scanned with an image-guided ultrasound probe. The region of interest may be located, for example, inside a human or animal. From 910, flow may move to 920.

In 920, visual image data such as ultrasound images and/or data may be received from the image-guided ultrasound probe of a peripheral region proximate to the region of interest. The image-guided ultrasound probe may include a first light-sensitive device and a second light-sensitive device attached at fixed positions relative to an ultrasound probe. The image-guided ultrasound probe may also output light from one or more LEDs, compact fluorescent lights, incandescent, or other light sources. The light from the light source may be diffused, using, for example, frosted glass, cellophane, fine mesh, or translucent adhesive tape (e.g., SCOTCH tape). From 920, flow may move to 930.

In 930, a tool may be employed for use within the region of interest and within the peripheral region such that at least a portion of the tool is visible to the first and second light-sensitive devices. The tool may be registered with the image-guided ultrasound probe imaging device. Registration may include showing the tool to the first and/or second light-sensitive devices. The position of the tool may then be known with respect to the imaging device. A representation of the tool may be displayed in a display. From 930, flow may move to 940.

In 940, the tool may be tracked or guided during the image-guided procedure based on imaging information from the first and second light-sensitive devices. The first and second light-sensitive devices may be attached to stabilization assembly 170 to prevent movement between the first light-sensitive device and the second light-sensitive device. The image-guided ultrasound probe may also include memory device 810 configured to store calibration, configuration, licensing, and/or usage data. In one embodiment, licensing data may be retrieved from the memory device. The licensing data may include includes a licensing period being an amount of usage of the image-guided ultrasound probe, an amount of elapsed time (with or without usage), or a calendar date. The usage data (including usage time) may be retrieved from the memory device. The licensing period may be compared with the retrieved usage time or calendar date. A licensing alert or warning may be displayed when usage time exceeds a specified percentage (e.g., absolute (duration or relative) or threshold of the licensing period, for example. From 940, flow may move to 950.

In 950, visual image data from the image-guided ultrasound probe may be displayed. Visual image data may include detected images from the human or animal body as well as calculated images of the tool or information about the tool. From 950, flow may move to 960.

In 960, a selection may be received of a target in the displayed visual image data. The target may be, for example, a tumor in the human or animal body. The target may be selected, for example, by using a touch screen display, the touch screen display may be showing images from the human or animal body including the tumor. From 960, flow may move to 970.

In 970, the tool may be guided to the selected target or close to the selected target. Guidance may include providing on-screen guidance to assist an operator in guiding a tool to the selected target. Or guidance may include displaying positioning assisting information to assist in positioning the tool close to the target. Two views may be displayed representing input of the first light-sensitive device and the second light-sensitive device. In the event the tool is unable to be tracked, an audio alert may sound and/or visual alert may be displayed. From 970, flow may move to 980.

In 980, an audible and/or visual signal may indicate the distance of the tool to the selected target. The distance may be indicated by the actual distance in units/numbers on the screen. Distance may also be indicated audibly by a series of tones that may increase in pitch and/or volume as the distance between the tool and the selected target decreases. From 980, flow may move to 990.

In 990, a quality of the tool tracking may be displayed. Quality of the tracking may be indicated by audible tones or visually through colors on the display. Quality of the tool tracking may also be represented by a length of a displayed line, where the displayed line may represent the tool being tracked. A loss of tool tracking (e.g., audio and/or video) may also be indicated or displayed. The quality of the tool tracking may be represented by an indicator such as the length of a displayed line or a color-coded element. From 990, flow may end.

In an embodiment, tracking of a medical tool (e.g., needle, surgical instrument) may be accomplished through one or more visible features on the tool. (Basic tool tracking has been described in previous publications by the inventors, such as Stolka et al. "Navigation with local sensors in handheld 3D ultrasound: initial in-vivo experience," SPIE Medical Imaging 2011, Lake Buena Vista, Fla./USA, pp. 79681J-79681J. International Society for Optics and Photonics, 2011, and Wang et al. "The Kinect as an interventional tracking system," SPIE Medical Imaging, San Diego, Calif., USA, pp. 83160U-83160U. International Society for Optics and Photonics, 2012, both of which are included by reference in their entirety.) The visible feature may include a detectable pattern, the pattern being initially created using a pseudo random binary sequence, or more generally a de Bruijn sequence, wherein the pattern is one of marked, printed, etched, or applied to the tool. The pattern may be used to detect insertion depth of the tool into a human or animal body. Alternatively, the visible feature may include an attachment such as a ring attached to the tool. The ring may be reflective and/or cylindrical or handle shaped. The ring may include a detectable pattern used in calculating an insertion depth of the tip of the tool, the detectable pattern may be initially created using a pseudo random binary sequence. Imaging system 200 may initially calculate a distance from the ring to the tip of the tool and use this calculated distance to calibrate the imaging system 200 for tool tracking.

The displayed information to assist in medical tool positioning may include information about the length of intersection between the medical tool and the non-infinitesimally thin ultrasound imaging plane, by drawing markers on the medical tool line to denote the extent of said intersection. In other words, a line may indicate the medical tool trajectory, wherein a portion of the line may be shaded differently to indicate the area where the medical tool will cross the imaging plane of the ultrasound Insertion depth calculation may be made based on the one or more visible features on the tool. Because of the nature of the visible feature, the insertion depth of the tip of the tool may be correctly calculated even when a portion of the one or more visible features is not viewable by the one or more light sensitive devices. For example, when the visible feature includes the detectable pattern created using a pseudo random binary sequence, the pattern is non-periodic and unique over small segments. Therefore, even if a small portion of the pattern is visible, imaging system 200 may still calculate the insertion depth. Tool tip location may be calculated (e.g., candidate tip locations) using the one or more visible features. The calculated tip locations may be in a three dimensional plane and may be based on the insertion location, calculated insertion depth, and angle of entry of the medical tool. Insertion depth of the tool tip and possible tip locations may be displayed on augmented display 220. A surgeon or other medical personal may use the displayed information when performing an IGI, for example.

The following describes one possible technique of localizing the medical tool tip in stereo images using the pattern on the medical tool shaft in an embodiment. Given a pair of stereo images (left and right light-sensitive device images) and light-sensitive device calibration (intrinsic and extrinsic light-sensitive device parameters), the first step of tip localization is to rectify the left and right images. Next, the medical tool is detected in these images as straight lines centered at the middle of the shaft. In order to localize the tip of the medical tool in 3D, the medical tool line is reconstructed in 3D space. This line is then sampled with a constant delta providing a set of 3D points. These points are then projected back into the left and right images resulting in two sets of 2D points for the left and right rectified images. Then, the pixel intensities at these points are computed using interpolation. This will generate two intensity vectors with regular sampling. In the next step, the two intensity vectors are correlated against all possible "sub-patterns". A sub-pattern is a minimal continuous portion of the whole pattern that could be uniquely identified. For each sub-pattern, the location that maximizes correlation and the correlation value is recorded. The sub-patterns with the highest correlation value is selected in the left and right vectors. Since the offset of the sub-pattern with respect to the tip is known, the 3D location of the tip can be estimated. Note that left and right images provide two almost independent estimates of the tip location. As a verification step, the two estimated tip locations should be closer than a threshold. The final tip location is given as the weighted-average of these two estimated tip positions.

In another embodiment, light waves may be filtered by the one or more light sensitive devices to only allow light of a specific wavelength and to restrict light of other wavelengths. A coating may be applied to the medical tool or other tool that may be illuminated based on receiving light of a specific wavelength. The coating may produce or reflect a light of the specific wavelength. The reflected or produced light of a specific wavelength may be detected by the light sensitive devices. The reflected or produced light of a specific wavelength may reduce the occurrence of false positives. Further, the coating may only illuminate or produce light of a specific wavelength to reveal the detectable pattern. The possible tip locations and insertion depth of the tip of the medical tool or tool may be calculated based on based on the displayed detectable pattern of light in a specific wavelength.

Illustrative Computer System

Figure 10:
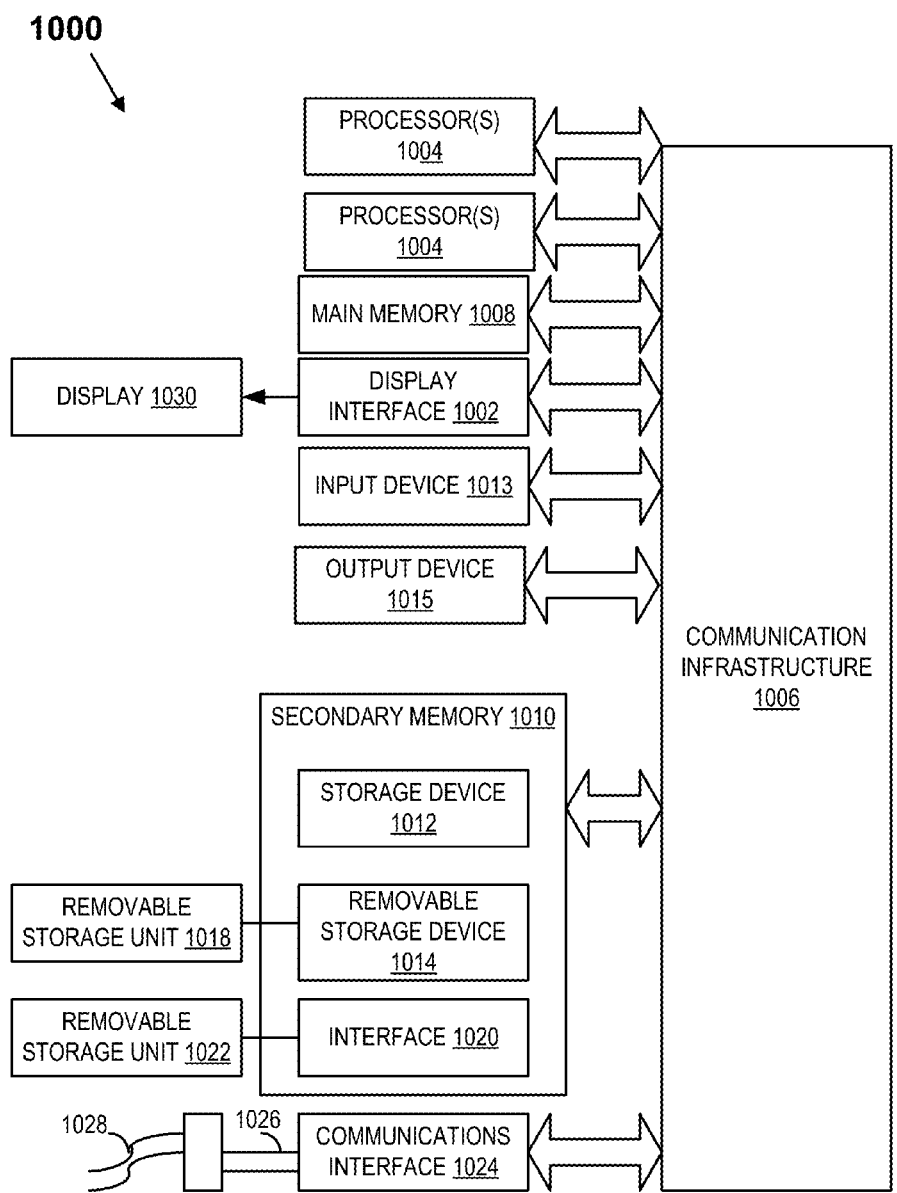
FIG. 10 depicts an illustrative embodiment of a computer for performing the methods and building the systems described herein.

FIG. 10 depicts an illustrative computer system that may be used in implementing an illustrative embodiment of the present invention. Specifically, FIG. 10 depicts an illustrative embodiment of a computer system 1000 that may be used in computing devices such as, e.g., but not limited to, standalone or client or server devices. FIG. 10 depicts an illustrative embodiment of a computer system that may be used as client device, or a server device, etc. The present invention (or any part(s) or function(s) thereof) may be implemented using hardware, software, firmware, or a combination thereof and may be implemented in one or more computer systems or other processing systems. In fact, in one illustrative embodiment, the invention may be directed toward one or more computer systems capable of carrying out the functionality described herein. An example of a computer system 1000 is shown in FIG. 10, depicting an illustrative embodiment of a block diagram of an illustrative computer system useful for implementing the present invention. Specifically, FIG. 10 illustrates an example computer 1000, which in an illustrative embodiment may be, e.g., (but not limited to) a personal computer (PC) system running an operating system such as, e.g., (but not limited to) MICROSOFT® WINDOWS® NT/98/2000/XP/Vista/Windows 7/Windows 8, etc. available from MICROSOFT® Corporation of Redmond, Wash., U.S.A. or an Apple computer or tablet executing MAC® OS, OS X, or iOS from Apple® of Cupertino, Calif., U.S.A., or a computer running a Linux or other UNIX derivative. However, the invention is not limited to these platforms. Instead, the invention may be implemented on any appropriate computer system running any appropriate operating system. In one illustrative embodiment, the present invention may be implemented on a computer system operating as discussed herein. An illustrative computer system, computer 1000 is shown in FIG. 10. Other components of the invention, such as, e.g., (but not limited to) a computing device, a communications device, a telephone, a personal digital assistant (PDA), an iPhone, an iPad, a Surface, and Android device, a 3G/4G wireless device, an LTE device, a wireless device, a personal computer (PC), a handheld PC, a laptop computer, a smart phone, a mobile device, a netbook, a handheld device, a portable device, an interactive television device (iTV), a digital video recorder (DVR), client workstations, thin clients, thick clients, fat clients, proxy servers, network communication servers, remote access devices, client computers, server computers, peer-to-peer devices, routers, web servers, data, media, audio, video, telephony or streaming technology servers, etc., may also be implemented using a computer such as that shown in FIG. 10. In an illustrative embodiment, services may be provided on demand using, e.g., an interactive television device (iTV), a video on demand system (VOD), via a digital video recorder (DVR), and/or other on demand viewing system. Computer system 1000 and/or parts of computer system 1000 may be used to implement the network, processing device, and/or components as described in FIGS. 1-3 and 5-8. Such as imaging component 100, printed circuit board 140, and/or other devices of imaging system 200.

The computer system 1000 may include one or more processors, such as, e.g., but not limited to, processor(s) 1004. The processor(s) 1004 may be connected to a communication infrastructure 1006 (e.g., but not limited to, a communications bus, cross-over bar, interconnect, or network, etc.). Processor 1004 may include any type of processor, microprocessor, or processing logic that may interpret and execute instructions (e.g., for example, a field programmable gate array (FPGA)). Processor 1004 may comprise a single device (e.g., for example, a single core) and/or a group of devices (e.g., multi-core). The processor 1004 may include logic configured to execute computer-executable instructions configured to implement one or more embodiments. The instructions may reside in main memory 1008 or secondary memory 1010. Processors 1004 may also include multiple independent cores, such as a dual-core processor or a multi-core processor. Processors 1004 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Computer system 1000 may include a display interface 1002 that may forward, e.g., but not limited to, graphics, text, and other data, etc., from the communication infrastructure 1006 (or from a frame buffer, etc., not shown) for display on the display unit 1001. The display unit 1001 may be, for example, a television, a computer monitor, or a mobile phone screen. The output may also be provided as sound through a speaker.

The computer system 1000 may also include, e.g., but is not limited to, a main memory 1008, random access memory (RAM), and a secondary memory 1010, etc. Main memory 1008, random access memory (RAM), and a secondary memory 1010, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory 1010 may include, for example, (but is not limited to) a hard disk drive 1012 and/or a removable storage drive 1014, representing a floppy diskette drive, a magnetic tape drive, an optical disk drive, a compact disk drive CD-ROM, flash memory, etc. The removable storage drive 1014 may, e.g., but is not limited to, read from and/or write to a removable storage unit 1018 in a well-known manner. Removable storage unit 1018, also called a program storage device or a computer program product, may represent, e.g., but is not limited to, a floppy disk, magnetic tape, optical disk, compact disk, etc. which may be read from and written to removable storage drive 1014. As will be appreciated, the removable storage unit 1018 may include a computer usable storage medium having stored therein computer software and/or data.

In alternative illustrative embodiments, secondary memory 1010 may include other similar devices for allowing computer programs or other instructions to be loaded into computer system 1000. Such devices may include, for example, a removable storage unit 1022 and an interface 1020. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 1022 and interfaces 1020, which may allow software and data to be transferred from the removable storage unit 1022 to computer system 1000.

Computer 1000 may also include an input device 1003 which may include any mechanism or combination of mechanisms that may permit information to be input into computer system 1000 from, e.g., a user. Input device 1003 may include logic configured to receive information for computer system 1000 from, e.g. a user. Examples of input device 1003 may include, e.g., but not limited to, a mouse, pen-based pointing device, or other pointing device such as a digitizer, a touch sensitive display device, and/or a keyboard or other data entry device (none of which are labeled). Other input devices 1003 may include, e.g., but not limited to, a biometric input device, a video source, an audio source, a microphone, a web cam, a video camera, a light-sensitive device, and/or other camera.

Computer 1000 may also include output devices 1015 which may include any mechanism or combination of mechanisms that may output information from computer system 1000. Output device 1015 may include logic configured to output information from computer system 1000. Embodiments of output device 1015 may include, e.g., but not limited to, display 1001, and display interface 1002, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. Computer 1000 may include input/output (I/O) devices such as, e.g., (but not limited to) input device 1003, communications interface 1024, cable 1028 and communications path 1026, etc. These devices may include, e.g., but are not limited to, a network interface card, and/or modems.

Communications interface 1024 may allow software and data to be transferred between computer system 1000 and external devices.

In this document, the terms "computer program medium" and "computer readable medium" may be used to generally refer to media such as, e.g., but not limited to, removable storage drive 1014, a hard disk installed in hard disk drive 1012, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to computer system 1000. It should be noted that a computer-readable medium that comprises computer-executable instructions for execution in a processor may be configured to store various embodiments of the present invention. References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may. The various embodiments described herein may be combined and/or features of the embodiments may be combined to form new embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product, such as, for example, a scientific modeling product. It may be downloadable from a network, for example, a website, as a stand-alone product or as an add-in package for installation in an existing software application. It may also be available as a client-server software application, or as a web-enabled software application. It may also be part of a system for detecting network coverage and responsiveness. A general purpose computer may be specialized by storing programming logic that enables one or more processors to perform the techniques indicated herein and the steps of, for example, FIG. 9.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application.

While various embodiments of the present invention have been described above, it should be understood that they have been presented by way of example only, and not limitation. Thus, the breadth and scope of the present invention should not be limited by any of the above-described illustrative embodiments, but should instead be defined only in accordance with the following claims and their equivalents.

We claim:

1. An image-guided ultrasound system, comprising:
   an ultrasound probe;
   a display configured to communicate with the ultrasound probe to receive ultrasound signals to display images from the ultrasound probe; and
   an imaging device at least one of removably attached to or integral with said ultrasound probe, the imaging device configured to communicate with an image processing module to process information derived from images from the imaging device, wherein the display receives and displays data from the image processing module, the imaging device comprising:
a rigid support and stabilization bar comprising a material with a low co-efficient of thermal expansion including a central portion coupled to one or more side portions,
an imaging device housing rigidly coupled to the central portion of the rigid support and stabilization bar,
a plurality of light-sensitive devices physically coupled to the one or more side portions of the rigid support and stabilization bar, a first light-sensitive device of the plurality of light-sensitive devices connected to one side portion of the support and stabilization bar and a second light-sensitive device of the plurality of light-sensitive devices connected to a different side portion of the rigid support and stabilization bar, wherein the rigid support and stabilization bar prevents mechanical and thermal movement between the first light-sensitive device, the second light-sensitive device, and the imaging device housing and forms a single stereo observation device,
at least one light source contained in the imaging device housing, the at least one light source operable to illuminate with light of a particular spectrum one or more tools observed by one or more of the plurality of light-sensitive devices,
a lens mounted in a viewing direction of one or more of the plurality of light-sensitive devices, said lens acting as a filter to allow only light of the particular spectrum into one or more of the plurality of light-sensitive devices, and
electronic memory physically coupled to the imaging device, the electronic memory configured to store at least one of calibration, configuration, and device identification, and further configured to store information for the imaging device, the information including at least one of:
elapsed time or usage since last calibration,
remaining time or usage until next calibration, or
next calibration date.

2. The system of claim 1, wherein the image processing module is configured to receive data from the ultrasound probe, the image processing module containing instructions executable on one or more processors, the instructions comprising:
receiving a selection of a target in the images from the ultrasound probe;
tracking a tool;
displaying the tool in the display;
calculating a distance between the tool and the target;
outputting audio, wherein audio changes are based on the calculated distance between the tool and the target; and
displaying the calculated distance between the tool and the target.

3. The system of claim 2, wherein the tool is a needle and the instructions further comprise:
indicating a needle tip in the display.

4. The system of claim 2, wherein the instructions further comprise:
displaying the tracked tool as a line; and
representing a quality of the tool tracking.

5. The system of claim 1, wherein the image processing module is configured to receive data from the ultrasound probe, the image processing module containing instructions executable on one or more processors, the instructions comprising:
tracking a tool;
displaying the tool in the display; and
outputting visual cues as to an observed length of the tracked tool observed by one or more of the plurality of light-sensitive devices.

6. The system of claim 1, wherein the image processing module is configured to receive data from the ultrasound probe, the image processing module containing instructions executable on one or more processors, the instructions comprising:
tracking a tool;
displaying the tool in the display; and
indicating a loss of visibility of the tracked tool by one or more of the plurality of light-sensitive devices through displaying visual alerts.

7. The system of claim 1, wherein the support and stabilization bar has a co-efficient of thermal expansion equal to or less than 22.2 $[10^{-6} (m/mK)]$.

8. The system of claim 1, wherein a surgical tool is registered with the imaging device, and a representation of the surgical tool is presented on the display.

9. A method for performing an image-guided procedure, comprising:
scanning a region of interest with an image-guided ultrasound probe;
receiving ultrasound data from said probe of a peripheral region proximate to said region of interest, wherein an imaging device housing is coupled to said probe, the imaging device housing containing a plurality of light-sensitive devices rigidly attached at fixed positions relative to each other and to the probe;
employing a tool for use within said region of interest and within said peripheral region such that at least a portion of said tool is visible to the plurality of light-sensitive devices;
enhancing visibility of said tool to one or more of the plurality of light-sensitive devices by:
illuminating said tool with light of a particular spectrum from at least one light source contained in the imaging device housing and
filtering light received by the one or more of the plurality of light-sensitive devices to allow only light of the particular spectrum; and
at least one of tracking or guiding said tool during said image-guided procedure based on imaging information from the plurality of light-sensitive devices,
wherein the plurality of light-sensitive devices are attached to a rigid support and stabilization bar comprising a material with a low co-efficient of thermal expansion including a central portion coupled to one or more side portions, the plurality of light-sensitive devices rigidly coupled to the one or more side portions, a first light-sensitive device of the plurality of light-sensitive devices connected to one side portion of the rigid support and stabilization bar and a second light-sensitive device connected to a different side portion of the rigid support and stabilization bar, the central portion rigidly connected to the imaging device housing, the support and stabilization bar preventing mechanical and thermal movement among each of the plurality of light-sensitive devices and between each of the plurality of light-sensitive devices and the imaging device housing, and wherein said probe further comprises electronic memory physically coupled to the imaging device, the electronic memory configured to store at least one of calibration, configuration, and device identification data, and further configured to store information for the imaging device, the information including at least one of:
elapsed time or usage since last calibration,
remaining time or usage until next calibration, or
next calibration date.

10. The method of claim 9 further comprising:
displaying the ultrasound data from the probe;
receiving a selection of a target in the displayed ultrasound data; and
display positioning assisting information to assist in positioning the tool close to the target and at least one of:
indicating a loss of visibility of the tracked tool by one or more light-sensitive devices of the plurality of light-sensitive devices through the displaying of a visual alert,
indicating audibly or visually a distance of the tool to a target, or
displaying visual cues as to an observed length of the tracked tool within an observation volume of the one or more light-sensitive devices.

11. The method of claim 9, further comprising:
displaying the ultrasound data from the probe;
receiving a selection of a target in the displayed ultrasound data; and
displaying positioning-assisting information to assist in positioning the tool close to the target, wherein the displayed positioning assisting information comprises displaying intersection information between the tool and a non-infinitesimally thin ultrasound imaging plane, wherein a displayed line represents a trajectory of the tool, and a non-zero length intersection of the tool trajectory and the imaging plane is visually represented by on the displayed line, wherein the visual representation denotes an extent of the intersection.

12. The method of claim 9, wherein the plurality of light-sensitive devices comprise one or more cameras, the method of claim 9 further comprising:
preventing interference from shadows by diffusing outputted light from the at least one light source.

13. The method of claim 12, wherein the at least one light source is diffused using a light diffuser, wherein the light diffuser is mounted directly in front of the at least one light source, wherein the at least one light source comprises at least one of LEDs, CFLs, incandescent bulbs, or lasers, and wherein the light diffuser comprises at least one of a pane of frosted transparent material, a pane of shaped transparent material, cellophane, fine mesh, or translucent adhesive tape.

14. The method of claim 9, further comprising at least one of:
retrieving the data on elapsed time or usage since last calibration from the electronic memory, and running a first check on whether said elapsed time or usage is less than a fixed maximum period;
retrieving the data on remaining time or usage until next calibration from the electronic memory, and running a second check on whether said remaining time or usage is greater than zero; and
displaying a calibration alert when the first check or the second check returns false.

* * * * *